United States Patent
Park et al.

(10) Patent No.: US 7,256,018 B2
(45) Date of Patent: Aug. 14, 2007

(54) MICROORGANISM PRODUCING L-THREONINE HAVING INACTIVATED TYRR GENE, METHOD OF PRODUCING THE SAME AND METHOD OF PRODUCING L-THREONINE USING THE MICROORGANISM

(75) Inventors: Young Hoon Park, Seongnam (KR); Byoung Choon Lee, Seoul (KR); Jae Yong Park, Gunpo (KR); Kwang Myung Cho, Icheon (KR); Yong Uk Shin, Seoul (KR)

(73) Assignee: CJ Corporation, Seoul (KR)

( * ) Notice: Subject to any disclaimer, the term of this patent is extended or adjusted under 35 U.S.C. 154(b) by 0 days.

(21) Appl. No.: 11/049,844

(22) Filed: Feb. 4, 2005

(65) Prior Publication Data

US 2005/0176113 A1    Aug. 11, 2005

(51) Int. Cl.
*C12P 1/00* (2006.01)
*C12P 21/04* (2006.01)

(52) U.S. Cl. ............... 435/71.2; 435/41; 435/45; 435/71.1

(58) Field of Classification Search ............... None
See application file for complete search history.

(56) References Cited

FOREIGN PATENT DOCUMENTS

| EP | 1 347 057 A | 9/2005 |
|---|---|---|
| JP | 05-344881 A | 12/1993 |
| KR | 9 208 365 B | 9/1992 |

OTHER PUBLICATIONS

Cummings L, Riley L, Black L, Souvorov A, Resenchuk S, Dondoshansky I, Tatusova T. Genomic BLAST: custom-defined virtual databases for complete and unfinished genomes. FEMS Microbiol Lett. Nov. 5, 2002;216(2):133-8.*
NCBI genomic BLAST with microbial genomes pp. 1-11.*
Mims et al., Medical Microbiology Third EditionElsevier Science, 2004, pp. 280-282.*
Ajdic D, Ferretti JJ.Regulation of the galactose operon of *Streptococcus mutans*. Adv Exp Med Biol. 1997;418:1015-8. PMID: 9331823 (Abstract).*
Neidhardt et al., *Escherichia coli* and Salmonella: Cellular and Molecular Biology, Second Edition: Two Volumes, 1996, pp. 357-387.*
J. Yang et al., "Molecular Analysis of the Regulatory Region of the *Escherichia coli* K-12 *tyrB* Gene," *J. Bacteriology*, 169 (10):4710-4715 (1987).
R.A. Jensen, "Evolution of Metabolic Pathways in Enteric Bacteria," in *Escherichia coli* and Salmonella: cellular and molecular biology, $2^{nd}$ edn. ASM Press. Washington, DC, (1996) pp. 2649-2662.
E. McFall et al., "Amino Acids as Carbon Sources," in *Escherichia coli* and Salmonella: cellular and molecular biology, $2^{nd}$ edn. ASM Press. Washington, DC (1996) pp. 358-379.
F.R. Blattner et al., "The Complete Genome Sequence of *Escherichia coli* K-12," *Science* 277:1453-1462 (1997).
G. Pozzi et al., "Competence for Genetic Transformation in Encapsulated Strains of *Streptococcus pneumoniae*:Two Allelic Variants of the Peptide Pheromone," *J. Bacteriology*, 178 (20): 6087-6090 (1996).
U. Güldener et al., "A New Efficient Gene Disruption Cassette For Repeated Use in Budding Yeast," *Nucleic Acids Research*, 24 (13):2519-2524, (1996).
Lee, Jin-Ho, et al., Global Analyses of Transcriptomes and Proteomes of a Parent Strain and an L-Threonine-Overproducing Mutant Strain, Journal of Bacteriology, Wash., D.C., vol. 185, No. 18, Sep. 2003, pp. 5442-5451, XP009022136.
Cornish, E.C., et al., "Structure of the *Escherichia coli* K12 Regulatory Gene tyrR" Nucleotide Sequence and Sites of Initiation of Transcription and Translation, Journal of Biological Chemistry, vol. 261, No. 1, 1986, pp. 403-410, XP002343281.
Shang L, Fan C-S, Jin R-L, Liu D-X, Wang J-G, "Knockout of tyR Gene in *Escherichia coli* and Its Effects on the Phenylalanine Biosynthesis," *Acta Biochemica et Biophysica Sinica*, 2003, 35(8): 728-733.

* cited by examiner

*Primary Examiner*—Joseph Woitach
*Assistant Examiner*—Maria Leavitt
(74) *Attorney, Agent, or Firm*—Rothwell, Figg, Ernst and Manbeck

(57) ABSTRACT

Provided are a microorganism capable of producing L-threonine and having an inactivated tyrR gene, a method of producing the same and a method of producing L-threonine using the microorganism. The microorganism can be used to produce L-threonine in high yield.

3 Claims, 2 Drawing Sheets

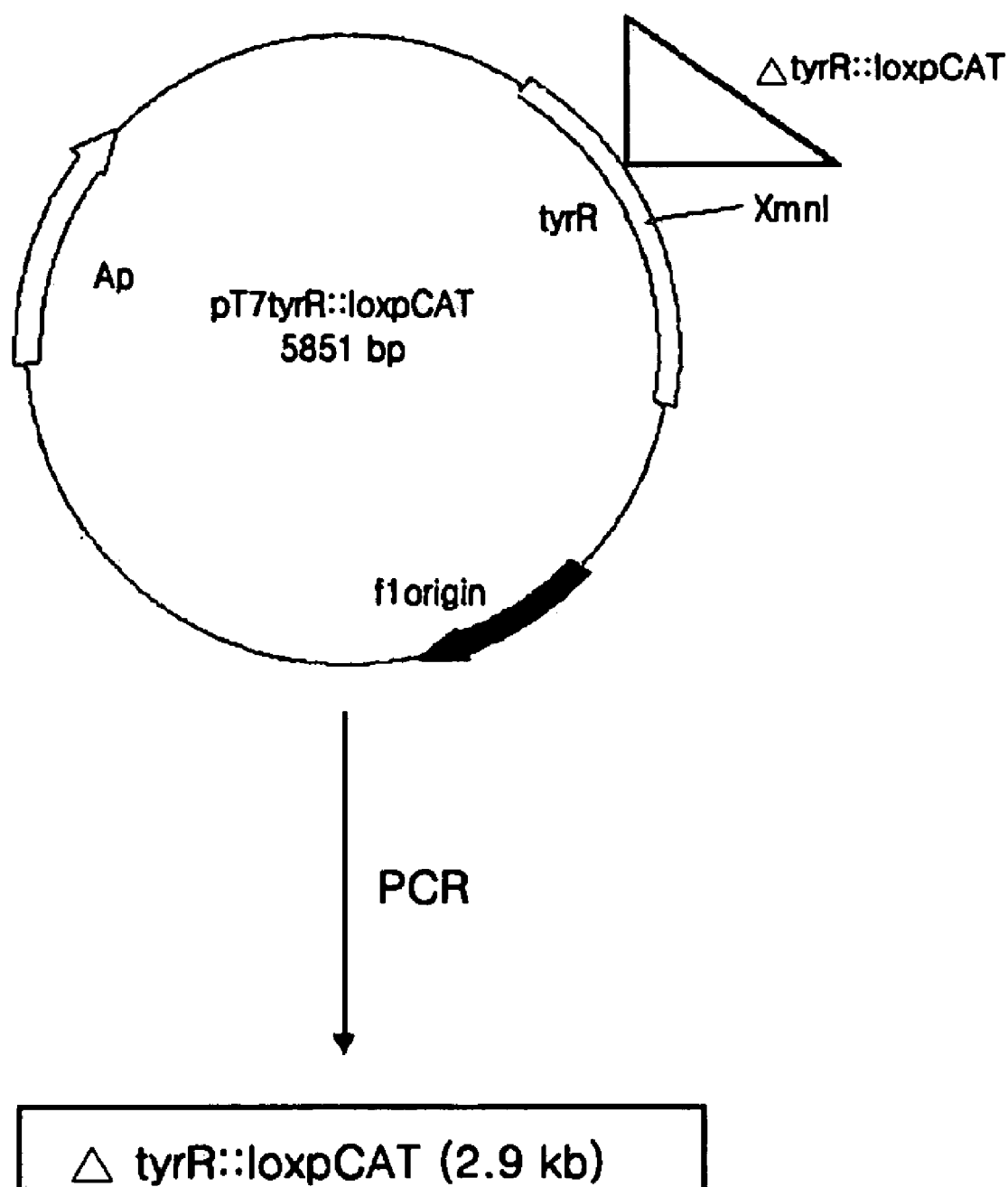

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
gcccgctgcc gtggattgac gat                                    23

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
agtttgcgcg tgctgggata attg                                   24

MICROORGANISM PRODUCING L-THREONINE HAVING INACTIVATED TYRR GENE, METHOD OF PRODUCING THE SAME AND METHOD OF PRODUCING L-THREONINE USING THE MICROORGANISM

BACKGROUND OF THE INVENTION

This application claims the benefit of Korean Patent Application No. 10-2004-0007528, filed on Feb. 5, 2004, in the Korean Intellectual Property Office, the disclosure of which is incorporated herein in its entirety by reference.

1. Field of the Invention

The present invention relates to a microorganism having an inactivated tyrR gene, a method of producing the same and a method of producing L-threonine using the microorganism.

2. Description of the Related Art

L-threonine is an essential amino acid and is widely used as a feed and food additive, and also as a pharmaceutical and raw material for synthesizing some drugs. It has been produced by fermentation with artificial mutants of the genus *Escherichia, Coryneform* bacteria, *Seratia* and *Providencia*. For example, Japanese Patent Publication No. 10037/81 discloses a method of producing L-threonine using a strain belonging to the genus *Escherichia* which has a requirement for diaminopimelic acid and methionine, and has the resistance to the feedback inhibition by threonine of the biosynthetic system of threonine. Japanese Patent Application Laid-open No. 224684/83 discloses a method of producing L-threonine using a strain belonging to the genus *Brevibacterium* which is resistant to S-(2-aminoethyl)-L-cysteine and α-amino-β-hydroxy valeric acid and has a nutritional requirement for L-isoleucine and L-lysine. Korean Patent Application Laid-open No. 8022/87 discloses a method of producing L-threonine using a diaminopimelic acid and methionine-requiring, α-amino-β-hydroxy valeric acid-resistant strain belonging to the genus *Escherichia* which has an additional resistance to at least one substance selected from the group consisting of rifampicin, lysine, methionine, aspartic acid, and homoserine, or has a reduced ability to decompose L-threonine. Japanese Patent Application Laid-open No. 219582/90 discloses a method for producing L-threonine using a strain belonging to the genus *Providencia* which is resistant to α-amino-β-hydroxy valeric acid, L-ethionine, thiaisoleucine, oxythiamine, and sulfaguanidine, and has a requirement for L-leucine and also a leaky requirement for L-isoleucine.

However, the above known methods have the disadvantages that they fail to afford a high production of L-threonine or require costly requirements such as diaminopimelic acid and isoleucine. In other words, the use of diaminopimelic acid-requiring strains in the production of L-threonine includes an additional fermentation of diaminopimelic acid and thus may increase cost. Where a strain having a requirement for isoleucine is used for the production of L-threonine, costly isoleucine must be added to fermentation media, which increases cost.

In an attempt to overcome these disadvantages, the present inventors developed an L-threonine-producing strain of *Escherichia coli* which is resistant to L-methionine, L-threonine and L-lysine analogues and α-aminobutyric acid, and has a nutritional requirement for methionine and a leaky requirement for isoleucine. They successfully produced L-threonine by fermentation with the strain at higher yields than with prior strains. The strain and a method for producing L-threonine using said strain are disclosed in Korean Patent Publication No. 92-8365.

Oxidative decomposition of tyrosine has two routes, i.e. decomposition to fumarate and acetoacetate and decomposition after conversion into 3,4-hydroxyphenylacetate by tyrosinase. In the former case, L-tyrosine reacts with α-ketoglutarate to produce L-glutamate and 4-hydroxyphenylpyruvate (Neidhardt FC et al., (eds) *Escherichia coli* and *Salmonella:* cellular and molecular biology, $2^{nd}$ edn. ASM Press. Washington D.C., 1996, pp. 2649-2660). The biosynthesis of tyrosine and phenylalanine includes transamination. An important enzyme in the transamination is encoded by tyrB, aspC and ilvE genes (Ji Yang and James Pittard, Journal of Bateriology, 1987, 167, pp. 4710-4715). That is, the tyrB gene encodes a subunit of aromatic amino acid transaminase. A TyrB protein encoded by the tyrB gene is involved in the transamination by the aromatic amino acid transaminase in the third and final steps of tyrosine biosynthesis as the subunit (Neidhardt FC et al., (eds) *Escherichia coli* and *Salmonella:* cellular and molecular biology, $2^{nd}$ edn. ASM Press. Washington D.C., 1996, pp. 2649-2660). The tyr B gene also has a function similar to aspC gene to be involved in the synthesis of aspartate (ASP) from oxaloacetate (OAA) as well as the biosynthesis of tyrosine and phenylalanine. ASP is an intermediate for L-threonine biosynthesis (Neidhardt FC et al., (eds) *Escherichia coli* and *Salmonella:* cellular and molecular biology, $2^{nd}$ edn. ASM Press. Washington D.C., 1996, pp. 358-403).

The tyrB gene belongs to tyrR regulon and undergoes repression of expression during trasncription by a product encoded by tyrR gene (Ji Yang and James Pittard, Journal of Bateriology, 1987, 167, pp. 4710-4715).

The present inventors have intensively studied to select strains having an improved ability to produce L-threonine on the basis of conventional technologies and now discovered that L-threonine biosynthesis can be facilitated by inactivation of the tyrR gene.

SUMMARY OF THE INVENTION

The present invention provides a microorganism having an improved ability to biosynthesize L-threonine.

The present invention also provides a method of producing the microorganism.

The present invention also provides a method of efficiently producing L-threonine using the microorganism.

According to an aspect of the present invention, there is provided a microorganism capable of producing L-threonine and having an inactivated tyrR gene.

According to another aspect of the present invention, there is provided a method of producing a L-threonine-producing microorganisim, the method including: preparing an inactivated tyrR gene or a DNA fragment thereof; introducing the inactivated tyrR gene or the DNA fragment thereof into a microorganism capable of producing L-threonine to cause recombination with a tyrR gene present on a chromosome of the microorganism; and selecting microorganisms having an inactivated tyrR gene.

According to another aspect of the present invention, there is provided a method of producing L-threonine, the method including: culturing the microorganism as describe above; and isolating L-threonine from the culture.

BRIEF DESCRIPTION OF THE DRAWINGS

The above and other features and advantages of the present invention will become more apparent by describing in detail exemplary embodiments thereof with reference to the attached drawings in which:

FIG. 2 depicts a construction of DNA fragment ΔtyrR::loxpCAT from recombinant plasmid pT7bluetyrR::loxpCAT.

DETAILED DESCRIPTION OF THE INVENTION

Figure 1:
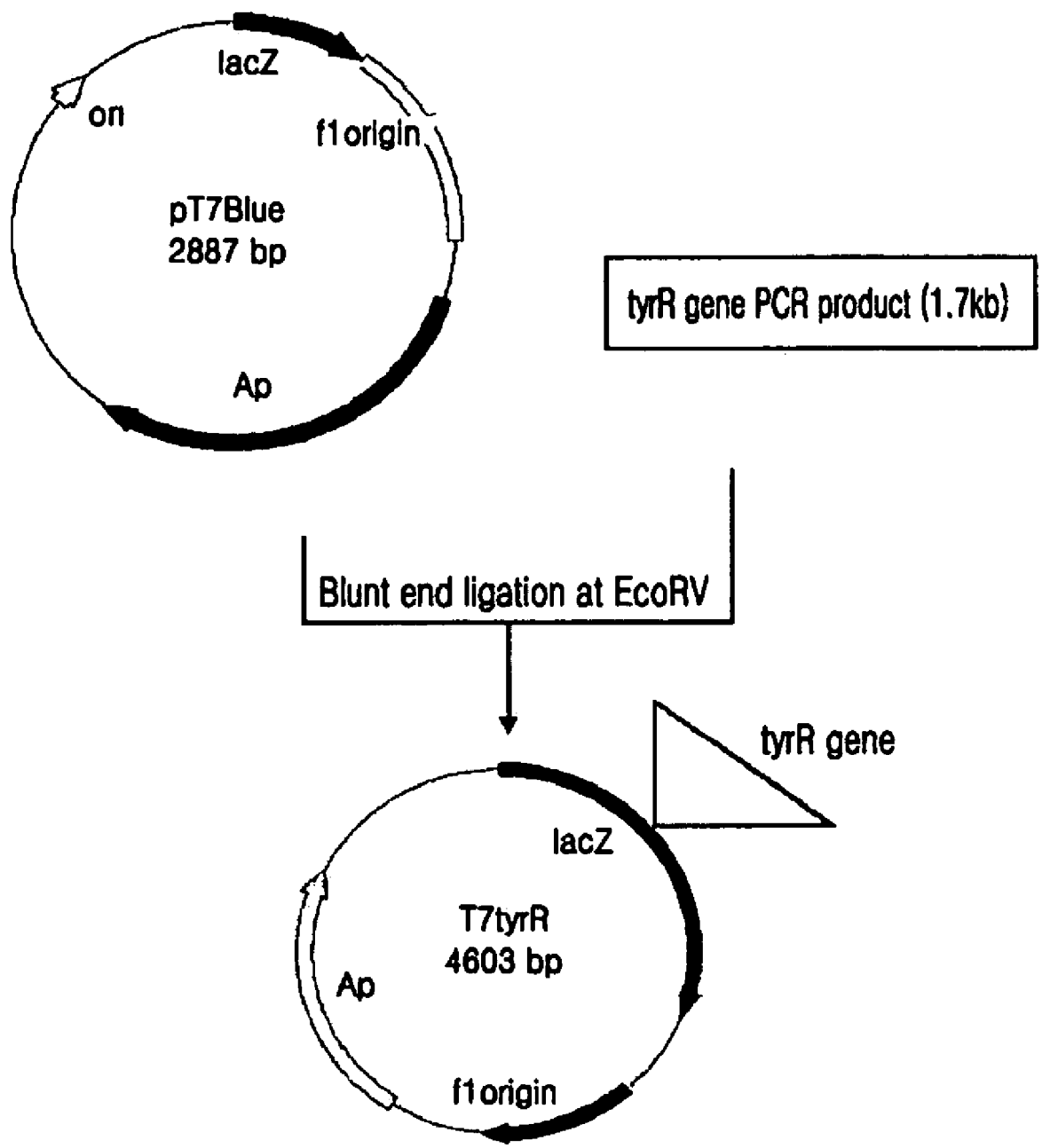
FIG. 1 depicts a construction of recombinant plasmid pTblue/tyrR including a tyrR gene.

The present invention provides a microorganism capable of producing L-threonine and having an inactivated tyrR gene.

In the present invention, the microorganism can produce L-threonine and includes prokaryotic and eukaryotic microorganisms having an inactivated tyrR gene. For example, strains belonging to the genus *Escherichia, Erwinia, Serratia, Providencia, Corynebacterium* and *Brevibacterium* can be included. Preferably, the microorganism belongs to the Enterobacteriaceae family and, more preferably, to the genus *Escherichia*. Most preferably, the microorganism is *Echerichia coli* FTR7624 (KCCM-10538).

Also, the microorganism may include L-threonine-producing mutants as well as natural microorganisms. Examples of the mutants include microorganisms belonging to L-threonine-producing *Escherichia coli* which are resistant to L-methionine, L-threonine and L-lysine analogues and α-aminobutyric acid, and have a nutritional requirement for methionine and a leaky requirement for isoleucine; and mutated microorganisms in which at least one copy of phosphoenol pyruvate carboxylase (ppc) gene and thrA, thrB, and thrC genes contained in a threonine operon is inserted in a chromosomal DNA, in addition to intrinsic ppc gene and genes in the threonine operon. The L-methionine analogue may be at least one compound selected from the group consisting of D,L-ethionine, Norleucine, α-methylmethionine and L-methionine-D,L-sulfoxymine. The L-threonine analogue may be at least one compound selected from the group consisting of α-amino-β-hydroxy valeric acid and D,L-threonine hydroxamate. The L-lysine analogue may be at least one compound selected from the group consisting of S-(2-aminoethyl)-L-cysteine and δ-methyl-L-lysine.

In the present invention, the tyrR gene encodes a protein repressing the transcription by tyrB encoding TyrB (aromatic amino acid transminase) which acts in the third and final steps of the biosynthesis pathway of tyrosine. For the *Escherichia coli*, the tyrR gene is known and can be obtained from genome sequence published by Blattner, et al. (Science 277: 1453-1462 (1997)) (Accession no: AAC74405). The genome sequence can also be obtained from National Center for Biotechnology Information (NCBI) in USA and DNA Data Bank of Japan (DDBJ). The tyrR gene also includes an allele generated by attenuation of genetic code or mutation. The "inactivation" as used herein refers to no-expression of an active tyrR protein. Thus, the inactivation of the tyrR gene leads to an increase in expression of the tyrB gene.

The microorganism of the present invention can be produced by inactivating a tyrR gene present on a chromosome of a microorganism capable of producing L-threonine. The inactivation method may include causing mutation using light, such as UV-ray, or chemicals and isolating strains having an inactivated tyrR gene from the mutants. The inactivation method also includes a DNA recombination technology. The DNA recombination may be achieved, for example, by injecting a nucleotide sequence or vector including a nucleotide sequence with homology to the tyrR gene into the microorganism to cause homologous recombination. The nucleotide sequence and vector injected may include a dominant selectable marker.

The present invention also provides a method of producing a L-threonine-producing microorganisim, including: preparing an inactivated tyrR gene or DNA fragment thereof; introducing the inactivated tyrR gene or the DNA fragment thereof into a microorganism capable of producing L-threonine to cause recombination with a tyrR gene present on a chromosome of the microorganism; and selecting the microorganism having an inactivated tyrR gene.

The "inactivated tyrR gene or DNA fragment thereof" as used herein refers to a polynucleotide sequence having a sequence homology to the tyrR gene in a host but being unable to express an active tyrR protein due to loss, displacement, truncation and inversion. The introduction of the inactivated tyrR gene or DNA fragment thereof into a host cell can be achieved, for example, by transformation, conjugation, transduction or electroporation, but is not limited thereto.

When the inactivated tyrR gene or DNA fragment thereof is introduced into the host cell by transformation, the inactivation procedure can be carried out by mixing the polynucleotide sequence with a culture of the strain. While the strain is naturally competent for DNA uptake to be transformed, it is preferred that the strain can be previously rendered competent for DNA uptake by any suitable method (See e.g. LeBlanc et al., Plasmid 28, 130-145, 1992; Pozzi et al., J. Bacteriol. 178, 6087-6090, 1996). The inactivated tyrR gene or DNA fragment thereof has a foreign DNA piece introduced in a genome DNA fragment and replaces the wild-type chromosomal copy of the sequence with an inactivated state. In an embodiment of the present invention, the inactivated polynucleotide sequence includes "tails" comprising a part of the target site DNA at the 5' and 3' ends thereof. The tails should be at least 50 base pairs and preferably greater than 200 to 500 base pairs for efficient recombination and/or gene conversion. For convenience, the inactivated polynucleotide sequence can include a selectable marker, for example, an antibiotic resistance gene. Where the target DNA is disrupted with an antibiotic resistance gene, selection of transformants is carried out on agar plates containing suitable levels of an appropriate antibiotic. Following transformation, the inactivated polynucleotide sequence introduced into the host cell undergoes homologous recombination with the genomic DNA tails, resulting in inactivation of the wild-type genomic sequence. Inactivation recombination events are easily confirmed by, for example, Southern blotting, or more conveniently by polymerase chain reaction (PCR).

In an embodiment of the present invention, a method of producing the L-threonine-producing microorganism of the present invention comprises the following procedures.

First, genomic DNA is isolated from a strain that is capable of producing L-threonine and PCR is performed using it as a template by a conventional technology to amplify the tyrR gene.

Next, the obtained tyrR gene is cloned into a suitable plasmid or other vector. The recombinant vector is introduced by transduction into a host cell such as *E. coli*. After the transformant is grown and cells are isolated, the recombinant vector having tyrR genes is extracted. An antibiotic resistant gene fragment is then inserted into the tyrR gene of the extracted recombinant vector to form a recombinant vector having an activated tyrR gene. This recombinant vector is introduced by transformation into a host cell and the host cell is cultivated in a suitable culture medium. Then, the propagated recombinant vector is isolated from the resultant transformant, and the polynucleotide sequence having an inactivated tyrR gene is obtained by suitable restriction enzyme digestion(s). Thereafter, this polynucleotide sequence is introduced into a host that is capable of producing L-threonine by a conventional technique such as electroporation. Microorganisms having an antibiotic resistance are selected to isolate microorganisms having an inactivated tyrR gene.

Skilled artisans will recognize that the inactivated polynucleotide sequence of this invention can be generated by general cloning methods. For example, PCR amplification methods using oligonucleotide primers targeted to the tyrR gene can be used. Methods for PCR amplification are widely known in the art (see e.g. PCR Protocols: A Guide to Method and Application, Ed. M. Innis et al., Academic Press (1990)). The PCR comprises genomic DNA, suitable enzymes, primers, and buffers, and is conveniently carried out in a DNA Thermal Cycler (Perkin Elmer Cetus, Norwalk, Conn. USA). A positive PCR result is determined by, for example, detecting an appropriately-sized DNA fragment following agarose gel electrophoresis.

In an embodiment of the present invention, recombinant plasmids pT7blue/tyrR and pT7bluetyrR::loxpCAT were prepared and an inactivated polynucleotide sequence ΔtyrR::loxpKAN was obtained therefrom. Then, an *Escherichia coli* strain that is resistant to L-methionine, L-threonine and L-lysine analogues and α-aminobutyric acid and has a nutritional requirement for methionine and a leaky requirement for isoleucine, namely *Escherichia coli* Accession No. KCCM 10236, was transformed with the inactivated polynucleotide sequence ΔtyrR::loxpKAN by electroporation. As a result, the wild-type tyrR gene is inactivated to a novel strain capable of producing a higher concentration of L-threonine than the prototype strain. The novel strain was designated as *Escherichia coli* FTR7624 and was deposited under the Budapest Treaty to the Korean Culture Center of Microorganisms on Dec. 4, 2003 and assigned Accession No. KCCM-10538.

*Escherichia coli* FTR7624 was derived from *Escherichia coli* Accession No. KCCM 10236 which was derived from *Escherichia coli* TF4076. The *Escherichia coli* TF4076 (KFCC10718) requires methionine and has resistance to threonine analogues (for example, α-amino-β-hydroxy valeric acid, AHV), lysine analogues (for example, S-(2-aminoethyl-L-cysteine, AEC), isoleucine analogues (for example, α-aminobutyric acid), methionine analogues (for example, ethionine) and the like. *Escherichia coli* Accession No. KCCM TF4076 is described in Korean Patent Publication No. 92-8365 which is incorporated herein in its entirety by reference. Phosphoenol pyruvate (PEP) is a precursor of oxaloacetate which is an intermediate of L-threonine biosynthesis pathway. The ppc gene and threonine operon originated from the chromosomes of *Escherichia coli* Accession No. KCCM TF4076 were amplified by the PCR and were additionally integrated into the chromosomes of *Escherichia coli* Accession No. KCCM TF4076 to generate *Escherichia coli* Accession No. KCCM 10236. Thus, *Escherichia coli* Accession No. KCCM 10236 possesses two ppc genes and two threonine operons. *Escherichia coli* Accession No. KCCM 10236 is, therefore, capable of expressing higher levels of the ppc genes catalyzing the formation oxaloacetate from PEP and the enzymes necessary for threonine biosynthesis from aspartate (thrA: aspartokinaze I-homoserine dehydrogenase, thrB: homoserine kinase, thrC: threonine synthase), thereby enabling an increase in L-threonine production.

The present invention also provides a method of producing L-threonine, including: culturing the microorganism capable of producing L-threonine and having an inactivated tyrR gene; and isolating L-threonine from the culture.

In the production method of L-threonine, the culturing may be carried out in a suitable culture medium under suitable culturing conditions known in the art and may be readily adjusted according to the type of strain selected by those skilled in the art. The culturing may be carried out by batch operation, continuous operation, or fed-batch operation (see e.g. "Biochemical Engineering" by James M. Lee, Prentice-Hall International Editions, pp. 138-176).

The culture medium should properly meet the requirements according to the stain selected. A variety of culture media are disclosed in literatures (see e.g. "Manual of Methods for General Bacteriology" by the American Society for Bacteriology, Washington D.C., USA, 1981). The culture medium contains carbon sources, nitrogen sources and trace amounts of ingredients. Examples of the carbon sources include carbohydrates such as glucose, sucrose, lactose, fructose, moltose, starch, cellulose; fats such as soybean oil, sunflower oil, castor oil, coconut oil; fatty acids such as palmitic acid, stearic acid, linoleic acid; alcohols such as glycerol and ethanol; and organic acids such as acetic acid. These carbon sources may be used alone or in combination. Examples of the nitrogen sources include organic substances such as peptone, yeast extract, meat extract, malt extract, corn steep liquor (CSL) and soybean; and inorganic substances such as urea, ammonium sulfate, ammonium chloride, ammonium phosphate, ammonium carbonate and ammonium nitrate. These nitrogen sources can be used alone or in combination. In the culture medium, phosphate sources such as potassium dihydrogenphosphate, dipotassium hydrogenphosphate, and corresponding sodium-containing salts can be included. Also, the culture medium can include metal salts such as magnesium sulfate or ferrous sulfate. In addition, amino acids, vitamins, and appropriate precursors can be included. The culture medium or precursor can be added to the culture in a batch or continuous way.

Ammonium hydroxide, potassium hydroxide, ammonia, phosphate or sulfuric acid, etc. is appropriately added to the culture during culturing to adjust pH of the culture. Also, an antifoaming agent such as fatty acid polyglycol ester is added to the culture to prevent the formation of foam. Culturing is carried out under aerobic conditions by injecting oxygen or oxygen-containing gas (e.g. air) to the culture. The culturing temperature is in the range of 20 to 45° C., preferably 25 to 40° C. The culturing can be continued until the desired amount of L-threonine is obtained, preferably for 10 to 160 hours.

L-threonine can be isolated from the culture by ordinary methods known in the art. The isolation methods include centrifuging, filtration, ion exchange chromatography and crystallization, etc. For example, the supernatant obtained by centrifuging the culture at a low speed to remove biomass can be isolated through ion exchange chromatography.

Hereinafter, the present invention will be described more specifically by examples. However, the following examples are provided only for illustrations and thus the present invention is not limited to or by them.

EXAMPLES

Example 1

Construction of Recombinant Plasmid and Knock-Out of tyrR Gene

In the present Example, a tyrR gene in a chromosome of *Escherichia coli* was knocked-out by homologous recombination. For this, a vector including a portion of the tyrR gene was prepared, and then was transformed into *Escherichia coli* host cell, followed by selecting strains having a knock-out tyrR gene.

Genomic DNA was extracted from L-threonine-producing *Escherichia coli* strain Accession No. KCCM 10236 by using the QIAGEN Genomic-tip System. The DNA fragment (about 1.7 kb) including ORF (open reading frame) of tyrR gene was amplified by PCR using the extracted genomic DNA as a template. The primers used were a pair of oligonucleotides (SEQ ID NO: 1 and SEQ ID NO: 2). PCR was performed by 30 cycles, each consisting of denaturation for 30 seconds at 94° C., annealing for 30 seconds at 60° C. and extension for 90 seconds at 72° C. in order.

The PCR product was loaded onto 1.0% agarose gel and subjected to electrophoresis. DNA was purified from the 1.7 kb tyrR gene band. The purified DNA was ligated to EcoRV site of cloning vector pT7Blue (Novagen Inc., USA) overnight at the temperature of 16° C. to construct the recombinant plasmid pT7Blue/tyrR (see FIG. 1). The resulting plasmid construct was transformed into *Escherichia coli* NM522. The transformed strain was plated on solid media containing 50 mg/L of carbenicillin and was cultured overnight at a temperature of 37° C.

The colonies formed were picked up with a platinum loop and inoculated into 3 ml of liquid LB media containing carbenicillin. After overnight culturing, plasmid DNAs were extracted from the culture using QIAGEN Mini Prep Kit. The plasmid DNA extract was digested with the restriction enzyme Xmn I and confirmed the cloning of tyrR gene. The confirmed plasmid pT7Blue/tyrR was cleaved with the restriction enzyme Xmn I and DNA was purified from a band of about 4.6 kb in 0.8% agarose gel. The purified DNA was blunt-end ligated with about 1.2 kb fragment of the gene for chloramphenicol resistance including loxp region, which was obtained by digesting plasmid ploxpCAT2 (U. Guldenre et al, Nucleic Acid Research 24 (13), 1996, pp 2519-2524) with Hinc II restriction enzyme, to construct about 5.8 kb recombinant plasmid pT7ΔtyrR::loxpCAT (see FIG. 2).

*Escherichia coli* NM522 was transformed with the recombinant plasmid pT7ΔtyrR::loxpCAT. The resulting transformant was streaked out onto a solid LB medium plate containing 50 mg/L of carbenicillin and 50 mg/L of chloramphenicol and cultured overnight at 32° C. The colonies formed were picked up with a platinum loop and inoculated into 3 ml of liquid LB media containing carbenicillin and chloramphenicol. After overnight culturing, plasmid DNAs were extracted using QIAGEN Mini Prep Kit. The DNA fragment (about 2.9 kb) including ORF of tyrR gene and loxpCAT site was amplified by PCR using the extracted plasmid DNA as a template. The primers used were a pair of oligonucleotides (SEQ ID NO: 1 and SEQ ID NO: 2). PCR was performed by 30 cycles, each consisting of denaturation for 30 seconds at 94° C., annealing for 30 seconds at 60° C. and extension for 60 seconds at 72° C. in order.

The resulting DNA fragment ΔtyrR::loxpCAT was transformed into L-threonine-producing *Escherichia coli* strain Accession No. KCCM 10236 by electroporation and the resulting transformant was streaked out onto a solid LB medium containing chloramphenicol to select colonies having a knock-out tyrR gene. The selected colonies were tested for their production of L-threonine in flask cultures.

Example 2

L-threonine Production in Erlenmeyer Flask by Selected Strains

Thirty colonies selected in Example 1 were cultured in an Erlenmeyer flask containing the threonine titer medium given in Table 1 below, and L-threonine production was compared.

TABLE 1

| Threonine titer medium | |
|---|---|
| Ingredients | Concentration (per liter) |
| Glucose | 70 g |
| Ammonium sulfate | 28 g |
| KH$_2$PO$_4$ | 1.0 g |
| MgSO$_4$•7H$_2$O | 0.5 g |
| FeSO$_4$•7H$_2$O | 5 mg |
| MnSO$_4$•8H$_2$O | 5 mg |
| Calcium carbonate | 30 g |
| L-methionine | 0.15 g |
| Yeast extract | 2 g |
| pH 7.0 | |

Each colony was cultured overnight on LB solid medium in a incubator at 32° C. Then, one platinum loop of the culture was inoculated into 25 ml of the titer medium and cultured at 32° C. and 250 rpm for 48 hours.

L-threonine from the culture was analyzed by high performance liquid chromatography (HPLC). The analysis results are given in Table 2 below. It can be seen from the results that the prototype strain Accession No. KCCM 10236 produces 23 g/L L-threonine and *Escherichia coli* FTR7624 of the present invention in which tyrR gene has been knocked out produces 26 g/L L-threonine. Therefore, it was observed that the present transformed microorganisms increase the output of L-threonine up to about 8% in comparison to the prototype strain. The selected *Escherichia coli* FTR7624 was deposited to the Korean Culture Center of Microorganisms on Dec. 4, 2003 and assigned Accession No. KCCM-10538.

TABLE 2

| Flask titration test results of strains | | |
|---|---|---|
| Strain | KCCM 10236 | FTR7624 |
| L-threonine (g/L) | 23 | 26 |

As demonstrated by Examples, the ability to biosynthesizing L-threonine of microorganisms is improved by knock-out of tyrR gene. This is probably because expression of the tyrB gene is increased by the knock-out of the tyrR gene, thereby increasing the supply rate of aspartate (APP) which is an intermediate for L-threonine biosynthesis. However, the improvement in productivity of the microorganism is not based on only this mechanism.

As described above, the microorganism having an inactivated tyrR gene of the present invention can produce L-threonine by fermentation in high yield.

Also, according to the method of producing L-threonine of the present invention, high yield of L-threonine can be produced.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A microorganism of the Enterobacteriaceae family capable of producing L-threonine and having an inactivated tyrR gene, wherein said microorganism is *Escherichia coli* FTR7624 (KCCM-10538).

2. A microorganism of the Enterobacteriaceae family, wherein said microorganism is *Escherichia coli* FTR7624 (KCCM-10538), further comprising at least one copy of phosphoenol pyruvate carboxylase (ppc) gene and thrA, thrB, and thrC genes are inserted into a chromosomal DNA, in addition to intrinsic ppc gene and thrA, thrB and thrC genes.

3. A method for producing L-threonine comprising: culturing the microorganism of claim 1; and isolating L-threonine from the culture.

* * * * *